United States Patent [19]

Farber

[11] 4,119,776
[45] Oct. 10, 1978

[54] VINYL PHTHALIDE COLOR FORMERS

[75] Inventor: Sheldon Farber, Appleton, Wis.

[73] Assignee: NCR Corporation, Dayton, Ohio

[21] Appl. No.: 790,627

[22] Filed: Apr. 25, 1977

Related U.S. Application Data

[63] Continuation-in-part of Ser. No. 566,852, Apr. 10, 1975, Pat. No. 4,022,771.

[51] Int. Cl.$^2$ .................. B41M 5/22; C07D 491/02; C09B 23/00
[52] U.S. Cl. .................. 542/441; 542/432; 542/436; 542/437; 544/153; 544/345; 544/350; 544/405; 544/406; 544/355; 260/326.14 R; 260/326.16; 260/283 R; 260/296 H; 260/343.3 R; 260/326.25
[58] Field of Search .............. 542/441, 432, 436, 437; 544/153; 260/326.14 R; 282/27.5

[56] References Cited

U.S. PATENT DOCUMENTS

| | | | |
|---|---|---|---|
| 3,491,111 | 1/1970 | Lin | 260/326.14 R |
| 3,491,112 | 1/1970 | Lin | 260/326.14 R |
| 3,491,116 | 1/1970 | Lin | 260/326.14 R |
| 3,936,564 | 2/1976 | Miyazawa | 282/27.5 |
| 4,020,068 | 4/1977 | Farber | 282/27.5 |

OTHER PUBLICATIONS

Perjessy et al. Chem. Abstracts 75 (1971) #150959.
Kolsaker Chem. Abstracts 82 (1975) #30495.

Primary Examiner—Allen B. Curtis
Attorney, Agent, or Firm—J. T. Cavender; E. Frank McKinney

[57] ABSTRACT

A chromogenic compound of normally colorless form is disclosed having the following structural formula:

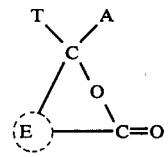

wherein A can be

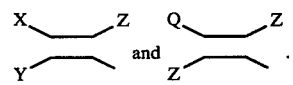

T, Q, X, Y and Z can be, among several others, hydrogen, alkyl, alkoxy, aryl, and heterocyclic, substituted and unsubstituted; and E can be a broad family of aromatic and heterocyclic structures. The compound is eligible for use in pressure-sensitive record materials and manifold marking systems. Because of light absorption characteristics, selected compounds of this invention are especially useful where machine readability and machine copiability are important.

10 Claims, 4 Drawing Figures

VINYL PHTHALIDE COLOR FORMERS

This application is a continuation-in-part of copending application Ser. No. 566,852 filed Apr. 10, 1975, issued as U.S. Pat. No. 4,022,771 on May 10, 1977.

BACKGROUND OF THE INVENTION

1. Field of the Invention

This invention pertains to colorable chromogenic compounds eligible for use in pressure-sensitive record material. Pressure-sensitive mark-forming record systems, single sheet and manifold, are improved by use of these compounds.

More specifically, this invention relates to chromogenic compounds having one vinyl linkage which compounds have the form of substantially colorless or slightly colored solids, or which approach being colorless when in liquid solution; but, which may be converted to dark-colored forms upon reactive contact with acidic material. As used in mark-forming systems, marking in desired areas on support webs or sheets may be accomplished by effecting localized reactive contact between the chromogenic material and the acidic material on or in such web or sheet, such material being brought thereto by transfer, or originally there in situ, the desired reactive contact forming dark-colored materials in the intended image-marking areas.

The chromogenic compounds of this invention have the following general formula:

wherein A can be

T, Q, X, Y, and Z can be, among several others, hydrogen, alkyl, alkoxy, aryl, and heterocyclic, substituted and unsubstituted; and E can be a broad family of aromatic and heterocyclic structures. More particularly, the compounds of this invention are represented by the following formulae:

(a)

wherein E is

X and Y are 4-methoxyphenyl, 4-(N-piperidino)phenyl and 4-(N-pyrrolidino)phenyl; and $R_1$, $R_2$, $R_7$ and $R_8$ are alkyl; provided when X is when X is

E is and when X is 4-methoxyphenyl, Y is X and E is (b)

wherein E is

-continued tetrachloro-substituted ;

X is ,

4-(N-piperidino)phenyl and 4-(N-pyrrolidino)phenyl;
Y is 4-(N-piperidino)phenyl, 4-(N-pyrrolidino)phenyl, phenyl and

;

$R_1$ is hydrogen, alkyl and phenyl;
$R_2$ is alkyl and cycloalkyl;
$R_3$ is hydrogen and alkoxy having 1 to 4 carbons; and
$R_7$ and $R_8$ are alkyl;
provided when Y is phenyl or wherein E is

,  and

; X is ,

4-(N-piperidino)phenyl, 4-(N-pyrrolidino)phenyl;
Y is any X, hydrogen and

;

$R_1$, $R_2$, $R_7$ and $R_8$ are alkyl; and
$R_3$ is hydrogen, methoxy, ethoxy and chlorine;
provided when E is or ,

$R_3$ is not chlorine, and additionally when Y is hydrogen or

, X is , and when E is ,

X is ,

Y is 4-(N-piperidino)phenyl, 4-(N-pyrrolidino)phenyl or and $R_3$ is chlorine;

(d)

wherein X is , 4-(N-piperidino)phenyl and 4-(N-pyrrolidino)phenyl;

Y is hydrogen, phenyl,  and

; and $R_1$, $R_2$, $R_7$ and $R_8$ are alkyl;

provided when Y is ,

X is ; and

-continued wherein T is kairol-6-yl and julolidin-9-yl;

wherein T is kairol-6-yl and julolidin-9-yl;

and $R_1$, $R_2$, $R_3$ and $R_8$ are alkyl.

The chromogenic compounds of this invention especially relate to marks at or near the near infrared part of the color spectrum; and, in that regard, especially relate to providing a color which is particularly visible to machine readers and copiers.

2. Description of the Prior Art

Several phthalide and fluoran chromogenic compounds have been disclosed. For example, U.S. Pat. Nos. 3,491,111 and 3,491,116, issued Jan. 20, 1970, disclose indole- and carbazol-substituted phthalides. U.S. Pat. No. 2,417,897, issued Mar. 25, 1947, discloses crystal violet lactone. U.S. Pat. No. 3,681,390, issued Aug. 1, 1972, discloses aryl-substituted fluorans.

U.S. Pat. No. 3,672,935, issued June 27, 1972, discloses use of colorless chromogenic compounds in pressure-sensitive record material.

G. Hallas, in the *Journal of the Society of Dyers and Colourists*, in Sept., 1967, at pages 368 to 373 and in June, 1970, at pages 237-242 discusses the effects of extended conjugation on colored dye compounds.

SUMMARY OF THE INVENTION

Colorable chromogenic compounds having one vinyl linkage have been discovered which compounds are initially substantially colorless but produce dark-colored products on reaction with certain acid materials. The vinyl-containing chromogenic compounds exhibit light absorption, in the colored form, at wavelengths nearer to infrared than chromogenic compounds without vinyl groups. It is an object of this invention to provide such vinyl-containing compounds and methods for making them.

An important use for the vinyl compounds of this invention resides in their incorporation into pressure-sensitive record systems as a colorable reactant for development of color on application of a mark-forming force. Hence, it is an object of this invention to provide substances having near infrared color response and chromogenic properties, which substances can be incorporated in a web or coated onto the surface of a web to provide a record sheet or a manifolding unit, and which are useful in carrying out methods of marking involving reactive contact with a color-activating material to develop dark-colored materials in areas where marking is desired.

It is an object of this invention to provide modified compounds, based upon the aforementioned vinyl-containing compounds, which are substantially colorless, or slightly colored, offering a variety of chromogenic characteristics, and developing dark-colored substances absorbing at increased wavelengths upon contact with color-activating materials.

BRIEF DESCRIPTION OF THE DRAWING

The chromogenic compounds of this invention include a large variety of several moieties with the vinyl linkages and lactone rings being necessarily common to all. In order to more completely and more distinctly disclose the variety of moiety combinations which forms a part of this invention, a drawing is included which is a schematic representation of the combinations, by structural formula.

Also included as drawings, are graphic representations of the absorption spectra of compounds of this invention compared with the spectra of similar compounds from the prior art.

Figure 1:
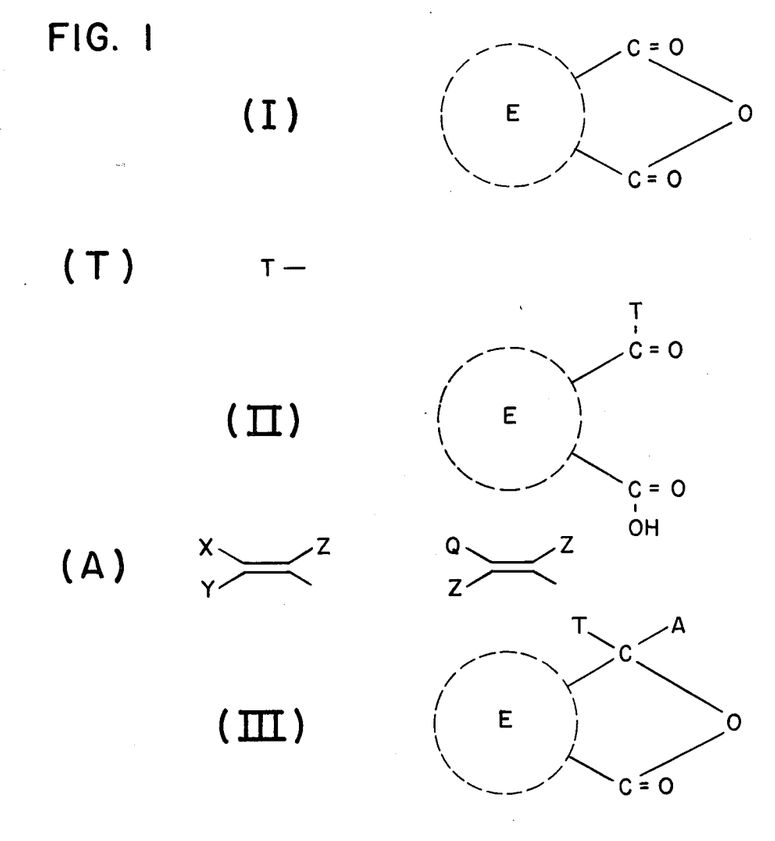

The drawing represents a figurative, schematic, step-by-step structural development of the vinyl-containing compounds of this invention, as they can be prepared. A dicarboxylic anhydride (I) is combined with a substrate reactant (T) to yield a keto acid (II), which is, in turn, combined with a vinyl-containing substrate reactant (A) to yield the chromogenic compound (III) of this invention. The structural development shown is not necessarily a representation of the actual compound synthesis. The synthetic process is not embraced as a part of this invention.

The dicarboxylic anhydride (I), in FIG. 1, includes E as the supporting molecular structure. E represents a large variety of structures including aromatic and heterocyclic, substituted and unsubstituted. The substitutions include halo, nitro, cyano, and alkylthio, alkoxy, alkyl, monoalkylamino and dialkylamino with alkyl of less than seven carbon atoms. Halogen or halo-, in this invention, means fluorine, chlorine, bromine and iodine. (I) is not required to be a dicarboxylic anhydride. A dicarboxylic acid will suffice if the keto acid-forming reaction is conducted under dehydrating conditions such as in acetic anhydride. Moreover, the vinyl-containing compound (A) can be a methyl carbinol under dehydrating conditions.

Figuratively speaking and in accord with the drawing, substrate moieties are added to the supporting molecular structure and at least one of the substrate moieties must contain a vinyl linkage. Substrate moieties are added at (T) to yield (II), a keto acid; and at (A) to yield (III), the compound of this invention.

(A) provides structural, schematic, indication of the manner in which vinyl linkages are introduced into the compounds of this invention. While there are differences between the specific moieties which will be disclosed in detail, below, it suffices to say, here, that X, Y, and Z represent, among other things, substituted and unsubstituted aromatic and heterocyclic groups as a part of the moieties of (A). Additionally, Q is exclusively a nitrogen heterocyclic and is joined to a carbon of the vinyl double bond at the nitrogen.

Figure 2:
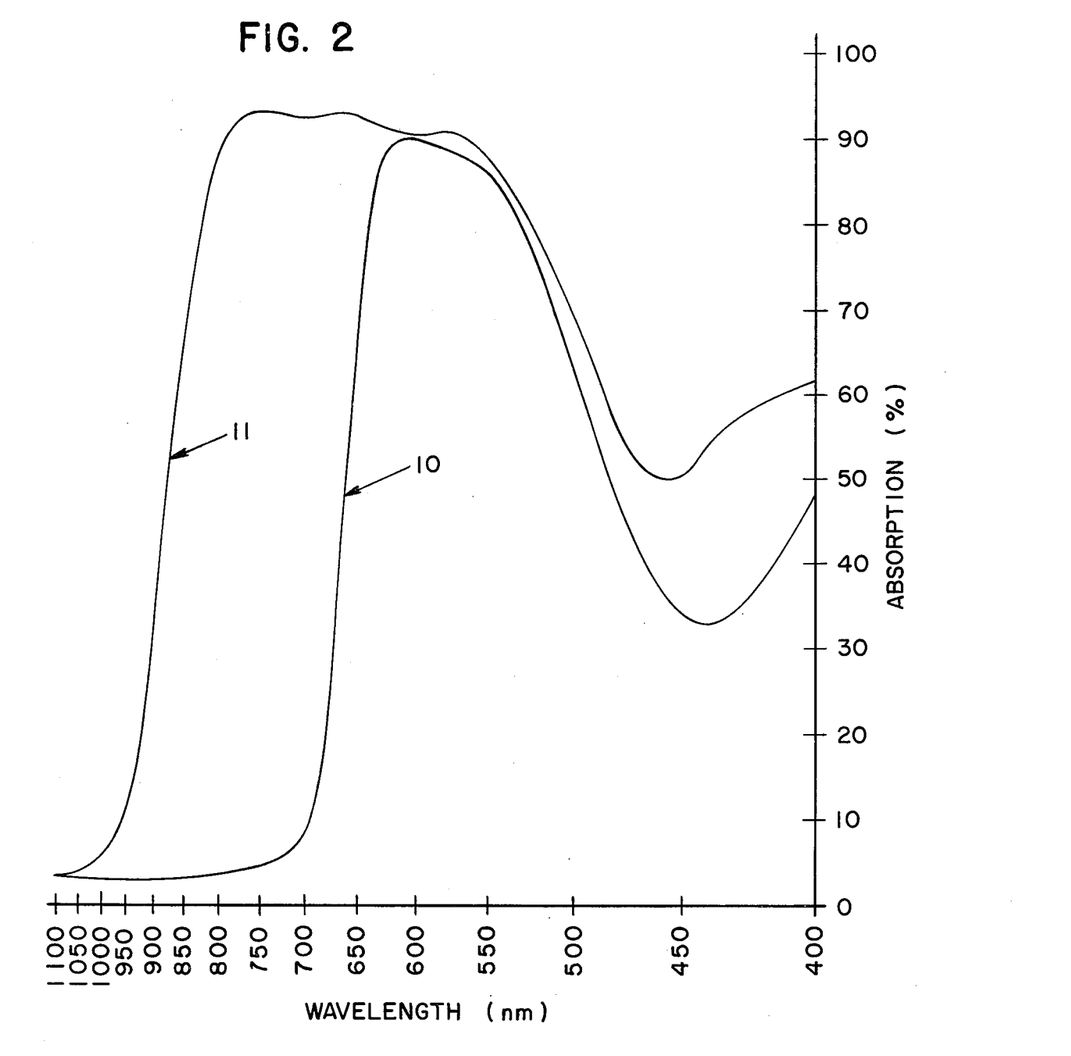
Figure 3:
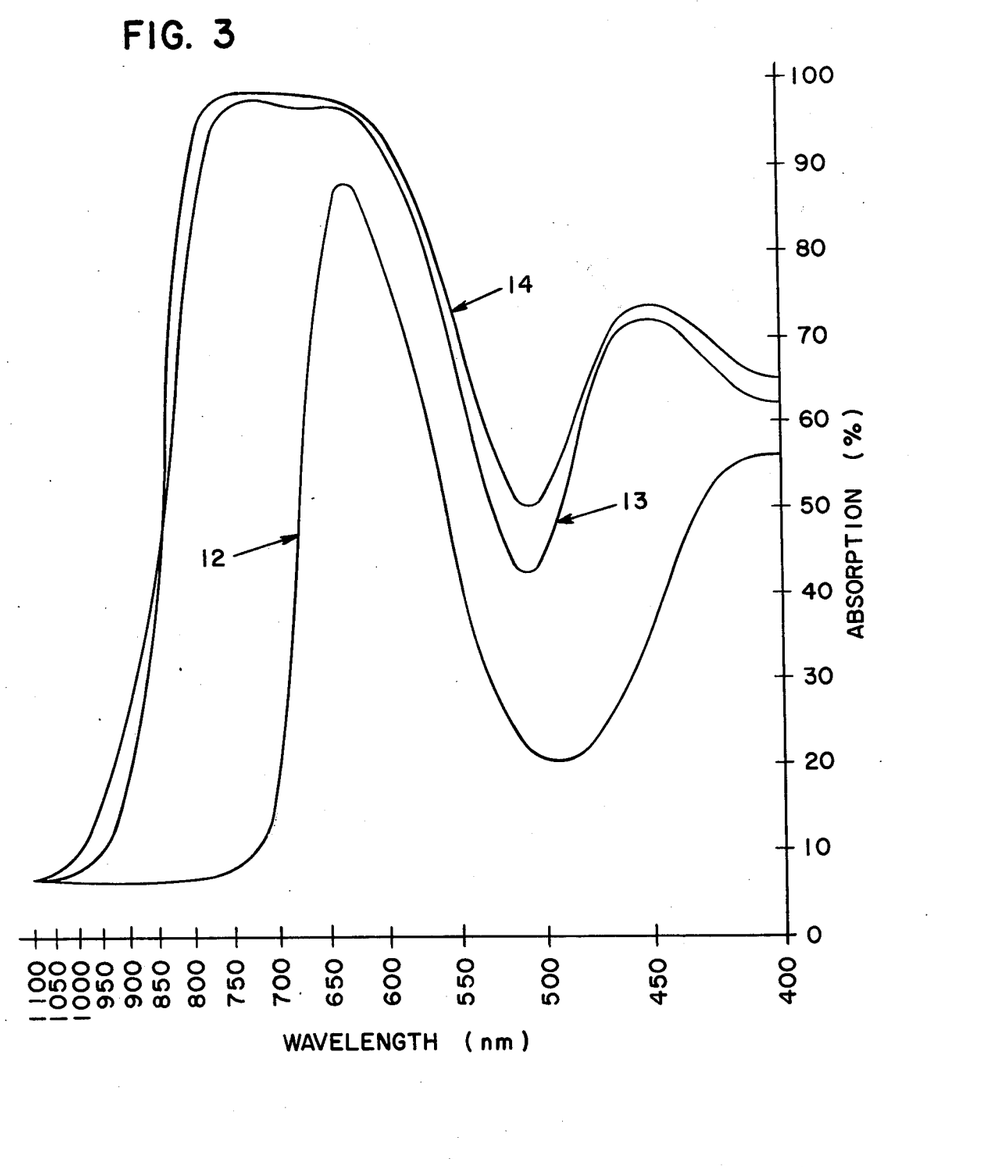
Figure 4:
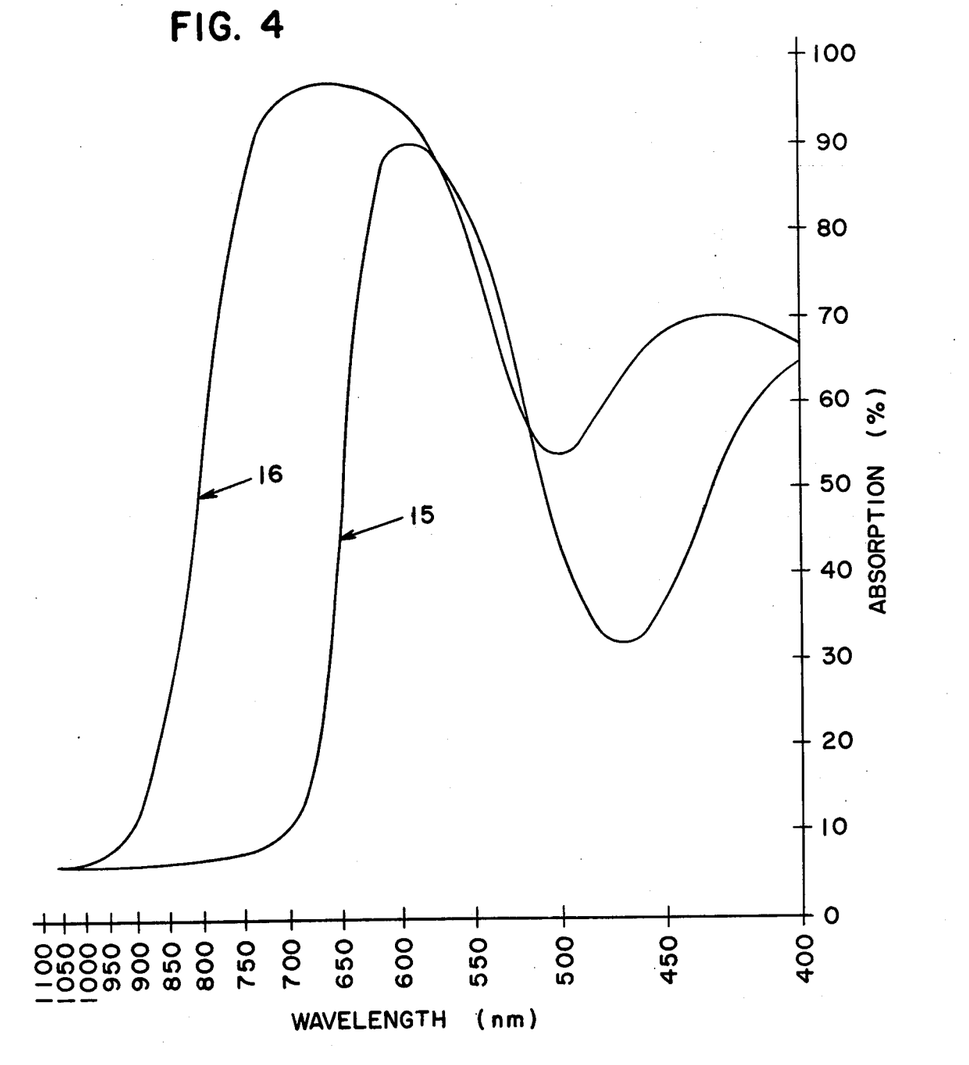

FIGS. 2 through 4 are comparative showings of the difference between reflectance of the colored form of the vinyl-containing compounds of this invention and the reflectance of similar compounds, but without the vinyl linkage, from the prior art. The abscissa in those graphical showings represents wavelength on a reciprocal scale and the ordinate represents percent of incident light absorbed. Throughout the consideration of this invention, it should be kept in mind that light visible to the human eye exists from about 400 to 700 nanometers wavelength and machine readers and copiers exhibit a maximum sensitivity at about 830 nanometers. FIGS. 2 through 4 indicate that, without exception, those compounds of this invention are remarkably more absorbent of light in the machine reading range than are prior art compounds.

The curves of FIGS. 2 through 4 represent the light absorption characteristics of selected chromogenic compounds, in colored form, as reacted from solution on a paper coated with a phenolic resin. In each figure, vinyl color formers of this invention are placed in comparative relation to compounds of the prior art having similar molecular structure or similar visible color; but without the vinyl element.

FIG. 2 is a comparison of the absorption spectrum of 3,3-bis-(4-dimethylaminophenyl)-6-(dimethylamino)phthalide (10), also known as crystal violet lactone, with the absorption spectrum of 3-(4-dimethylaminophenyl)-3-[bis-1,1-(p-dimethylaminophenyl)ethyleno-2]-6-dimethylamino phthalide (11), from Example 4, herein. The crystal violet lactone curve (10) has an absorption peak at about 625 nanometers (nm) which slopes to an ill-defined shoulder at about 515 nm and has strong absorption character between about 650 and 510 nm. In contrast, the 3-(4-dimethylaminophenyl)-3-[bis-1,1-(p-dimethylaminophenyl)-ethyleno-2]-6-dimethylaminophthalide curve (11) has an absorption peak at about 770 nm and strong secondary peaks at about 670 nm and 575 nm; and has strong absorption character between about 850 and 510 nm.

FIG. 3 is a comparison of the absorption spectrum of 3,3-bis-(4-dimethylaminophenyl)phthalide (12), also known as malachite green lactone, with the absorption spectra of 3-(4-diethylaminophen-1-yl)-3-[bis-1,1-(p-diethylaminophenyl)-ethyleno-2]phthalide (13), from Example 1, herein, and 3-(2-methoxy-4-diethylaminophenyl)-3-[bis-1,1-(p-dimethylaminophenyl)-ethyleno-2]phthalide (14), from Example 3, herein. The curve (12) has a rather sharp peak at about 640 nm while each of the curves (13) and (14) have a broad peak which extends from about 750 to about 640 nm.

FIG. 4 is a comparison of the absorption spectrum of 3-(1-ethyl-2-methylindol-3-yl)-3-(4-diethylaminophenyl)phthalide (15) with the absorption spectrum of 3-(1-ethyl-2-methylindol-3-yl)-3-[bis-1,1-(p-dimethylaminophenyl)ethyleno-2]phthalide (16), from Example 8, herein. The curve (15) has a relatively sharp peak at about 590 nm while the curve (16) has a broad peak from about 700 to about 630 nm.

DETAILED DESCRIPTION OF THE INVENTION

It should be remembered that what is considered to be an essential element of the invention herein is the presence of a vinyl linkage in a colorless but colorable chromogenic material. At the present time, the chromogenic compounds of this invention enjoy extensive eligibility for use in pressure-sensitive and thermally-sensitive mark-forming systems. Pressure-sensitive mark-forming systems provide a marking system of disposing on and/or within sheet support material unreacted mark-forming components and a liquid solvent in which each of the mark-forming components is soluble. The liquid solvent is present in such form that it is maintained isolated, by a pressure-rupturable barrier, from at least one of the mark-forming components until application of pressure causes a breach of the barrier in an area delineated by the pressure pattern. The mark-forming components are thereby brought into reactive contact, producing a distinctive mark.

The method of marking comprises providing a chromogenic compound selected from among the above-mentioned compounds and bringing such chromogenic compound into reactive contact, in areas where marking is desired, with an acidic color-activating substance to produce a dark-colored form of the chromogenic compound.

The acidic materials can be any compound within the definition of a Lewis acid, i.e., an electron acceptor. Preferably, acidic organic polymers such as phenolic polymers are employed as the acidic material. It is noted that the polymeric mark-forming components should have a common solubility with the chromogenic compound in at least one liquid solvent when the acid-reacting material is a phenolic or other organic acidic polymer. It is also noted that in a single system several chromogenic compounds can be used with the same or different polymeric materials. Several polymeric materials can be reactively contacted with a single chromogenic compound or with a mixture of chromogenic compounds.

The acidic polymeric material useful in this invention includes phenol polymers, phenol acetylene polymers, alkyl-phenolacetylene polymers, maleic acid-rosin resins, partially or wholly hydrolyzed styrene-maleic anhydride copolymers and ethylene-maleic anhydride copolymers, carboxy polymethylene and wholly or partially hydrolyzed vinyl methyl ether maleic anhydride copolymers and mixtures thereof.

When the acidic material is one of the aforementioned organic polymers, the liquid solvent chosen must be capable of dissolving the mark-forming components. The solvent can be volatile or non-volatile, and a single or multiple component solvent may be used which is wholly or partially volatile. Examples of volatile solvents useful in the aforedescribed basic chromogen-acidic polymer are toluene, petroleum distillate, perchloroethylene, xylene, and the like. Examples of non-volatile solvents are high-boiling point petroleum fractions, dioctyl adipate, biphenyls, diphenyl alkanes, and the like.

Generally, the solvent chosen should be capable of dissolving at least 0.3 percent, by weight, of the chromogenic compounds and at least about 3-5 percent, by weight, of the polymeric material. A further criterion of the solvent is that it must not interfere with the mark-forming reaction.

The support member on which the components of the system are disposed may comprise a single or dual sheet assembly. In the case where all components are disposed on a single sheet surface, the record material is referred to as a "self-contained" system. Where there must be a migration of the solvent, with or without mark-forming component, from one sheet to another, the record material is referred to as a "transfer" system. (Such a system can also be referred to as a "two-fold" system, in that at least two sheets are required and each sheet includes a component, or components, essential to the mark-forming reaction.) Where a copious amount of the colored reaction product in liquid form is produced on a surface of one sheet, it can produce a mark by transfer to a second sheet as a colored mark.

The polymeric material can be dissolved in ink composition vehicles to form a printing "ink" of colorless character and, thus, can be used to spot-print a proposed record sheet unit sensitized for recording in a reaction-produced color in those areas by application of a solution of the chromogenic material. In the case of phenolic polymer, a printing ink can be made of up to 75 percent, by weight, of the phenolic polymeric material in a petroleum solvent to a viscosity suitable for printing purposes.

In the mark-forming system herein, the acidic mark-forming component(s) reacts with the chromogenic material(s) to effect distinctive color formation or color change. In a multi-sheet system in which an acid organic polymer is employed, it is desirable to include other materials to supplement the reactants. For example, kaolin can be added to improve the transfer of the liquid and/or the dissolved materials between the sheets. In addition, other materials such as bentonite, attapulgite, talc, feldspar, halloysite, magnesium trisilicate, silica gel, pyrophyllite, zinc sulfide, calcium sulfate, calcium citrate, calcium phosphate, calcium fluoride, barium sulfate and tannic acid can be included. It should be noted that mineral materials such as kaolin, attapulgite, silica gel, silton clay, and the like can, also, be used alone or in combination with other materials as an acidic material coreactant.

Various methods known to the prior art and disclosed in the aforementioned U.S. Pat. No. 3,672,935 can be employed in coating compositions of the mark-forming materials into their supporting sheets. An example of the compositions which can be coated onto the surface of an underlying sheet of a two-sheet system to react with the chromogenic material on the underside of any overlying sheet is as follows:

| Coating Composition | Percent by Weight |
|---|---|
| Phenolic polymer mixture | 17 |
| Paper coating kaolin (white) | 57 |
| Calcium carbonate | 12 |
| Styrene butadiene latex | 4 |
| Ethylated starch | 8 |
| Gum arabic | 22 |
| | 100 |

Thermally-sensitive mark-forming systems can also be prepared using the compounds of this invention.

The compounds of this invention can be prepared as will be discussed in the examples which follow. Referring, again, to FIG. 1;—E can be the following:

, unsubstituted, and alkyl-, chloro-, dichloro-, trichloro-, tetrachloro-, bromo-, dibromo-, tribromo-, tetrabromo-, nitro-, and dialkylamino-substituted;

unsubstituted and nitro-substituted;

E can also be aromatic single anhydride residues such as result from homophthalic anhydride and biphenyl-4,4'-dicarboxylic anhydride

T can be the following: kairol-6-yl; julolidin-9-yl; 4-(N-morpholino)phenyl;

wherein $R_1$ and $R_2$ are hydrogen, alkyl, substituted phenyl, unsubstituted phenyl, benzyl, cycloalkyl, and acyl; $R_3$, $R_4$, $R_5$ and $R_6$ are hydrogen, alkyl, aryl, alkoxy, halo, aralkyl, dialkylamino, monoalkylamino, amino, acylamino, mercapto, and alkylthio; and $R_7$ and $R_8$ are hydrogen, phenyl and alkyl. $R_1$ and $R_2$ are not both phenyl. Q can be the following:

X can be the following:
4-(N-piperidino)phenyl;
4-(N-pyrrolidino)phenyl;

wherein the
R designations are the same as those earlier for T.
Y can be any X, hydrogen, phenyl and carbalkoxy.
Z can be hydrogen, halo, alkyl, carbalkoxy, benzyl, substituted phenyl, unsubstituted phenyl, and pyridino.
X or Y or both can also be 4-alkoxyphenyl; 2,4-dialkoxyphenyl; and 3,4-dialkoxyphenyl.

The definitions of E, T, X, Y, $R_1$, $R_2$, $R_3$, $R_7$, and $R_8$ should be considered with reference to each of the formulae (a) through (e) as modified by each of the respective provisos which modify the formulae. The full formulae and provisos are set forth in the specification under the section, Field of the Invention.

It should be understood that "alkyl" and any group requiring alkyl, such as "alkoxy" or "dialkylamino" means methyl, ethyl, propyl (including isopropyl), butyl (including isobutyl and tert-butyl), pentyl (including all five-carbon isomers), hexyl (including all six-carbon isomers), and the like having less than seven carbon atoms.

This invention is further illustrated by the following examples. The reactants and the proportions and other specific conditions are represented as being typical and should not be construed to limit the invention.

DESCRIPTION OF THE PREFERRED EMBODIMENTS

In the following examples, general procedures for preparing certain compounds of this invention are disclosed; and the procedures are followed by summaries of additional compounds prepared in the same manner. The summaries are not intended to be exhaustive and it must be remembered that the moieties, as previously defined, are all eligible for use in any combination in preparing the compounds.

EXAMPLE 1

Preparation of 3-(4-diethylaminophen-1-yl)-3-[bis-1,1-p-diethylaminophenyl)-ethyleno-2]phthalide.

With reference to the drawing in respect of this example and like examples which follow, the description of compound preparation commences at (II), the keto-acid, because preparation of the keto-acid is known or not difficult. For instance, the keto-acid of this example is easily prepared, either by mol-for-mol combination of phthalic anhydride (I) and N,N-diethylaniline (T), in the presence of a catalyst such as aluminum chloride or other Friedel-Crafts catalysts and in a solvent such as methylene chloride, or by the reaction of phthalic anhydride with m-diethylaminophenol followed by reaction of the keto-acid, thus obtained with dimethyl sulfate to etherify the hydroxyl group.

For ease in understanding, the Examples are summarized in listings of components, the (T) components are listed as radicals, and the (A) components are listed as compounds. Such listing is believed to facilitate comprehension of the molecular structures.

Combining the appropriate keto-acid, 2-(4-diethylaminobenzoyl)benzoic acid (II), with an appropriate ethylene base, results in a compound of this invention. This example will be given with details of the reaction conditions and will be followed by an additional listing of exemplary compounds. A mixture of 3.0 grams of the keto-acid (moiety II from I and T), 3.2 grams of bis-1,1-(p-diethylaminophenyl)ethylene (moiety A, wherein X and Y are p-diethylaminophenyl and Z is hydrogen), and 15 milliliters of acetic anhydride is refluxed for sixty minutes and poured into ice and ammonia. The system is extracted with toluene, dried in the toluene using sodium sulfate, and the toluene is evaporated. The residue is dissolved in toluene and chromatographed on alumina. The compound is eluted using toluene and is recrystallized from toluene-petroleum ether and then from toluene-heptane. The product exhibits a melting point of 122–124 degrees centigrade and a solution of the product imparts a greenish-blue color to paper coated with a phenolic resin or silton clay or a combination of the two. A reflectance spectrum of the greenish-blue color has unresolved absorption peaks at 750 and 660 nanometers. The Calculated analysis for $C_{40}H_{47}N_3O_2$, the title compound, is C, 79.83%; H, 7.8%; and N, 6.98%. Found, on analysis: C, 79.72%; H, 7.76%; and N. 7.15%.

This example is also conducted using bis-1,1-(p-di-t-butylaminophenyl)ethylene, bis-1,1-(2-ethoxy-4-dimethylaminophenyl)ethylene, bis-1,1-(2-methyl-4-diethylaminophenyl)ethylene or 2-ethyl-bis-1,1-(p-dimethylaminophenyl)ethylene. It should be pointed out that many of the ethylene compounds themselves are chromogenic compounds.

This example is also conducted using other anhydrides, such as 2,3-napthalene dicarboxylic acid anhydride, as the (I) moiety.

This example is also conducted using 2-methyl-bis-1,1-(p-diethylaminophenyl)ethylene and a different keto acid, 4-di-ethylamino-2-methoxy-2'-carboxy benzophenone.

A mixture of 1.55 grams of 4-diethylamino-2-methoxy-2'-carboxybenzophenone, 1.65 grams 2-methyl-bis-1,1-(p-diethylaminophenyl)ethylene and 5 milliliters of acetic anhydride is refluxed one minute. The reaction mixture is poured into a mixture of ice and ammonia and extracted with toluene. The layers are separated and the aqueous portion is washed with toluene. The toluene portions are combined and dried with sodium sulfate. The toluene solution is concentrated and subjected to alumina column chromatography. A non-crystalline product was obtained. A solution of the compound 3-(4-diethylamino-2-methoxyphenyl)-3-[2-methyl-bis-1,1-(4-diethylaminophenyl)ethyleno-2]phthalide imparts a green-blue color to paper coated with phenolic resin. A reflectance spectrum of the green-blue color has an absorption peak at about 630 nanometers.

Example 1, Summarized.

(I) phthalic anhydride
  (T) p-diethylaminophenyl
    (A) bis-1,1-(p-diethylaminophenyl)ethylene green-blue. absorption peak at 750 nanometers
    (A) bis-1,1-(p-methoxyphenyl)ethylene orange. absorption peak at 650 nanometers
    also (A) bis-1,1-(p-di-t-butylaminophenyl)ethylene
    also (A) bis-1,1-(2-ethoxy-4-dimethylaminophenyl)ethylene
    also (A) 2-ethyl-bis-1,1-(p-dimethylaminophenyl)ethylene
    (A) bis-1,1-(p-dimethylaminophenyl)ethylene green-blue. absorption peak at 770 nanometers
    (A) 2-carbethoxy-bis-1,1-p-dimethylaminophenyl)ethylene green. absorption peak at 640 nanometers
    also (A) 2-benzyl-bis-1,1-(p-dimethylaminophenyl)ethylene
    (A) 2-methyl-bis-1,1-(p-diethylaminophenyl)ethylene green. absorption peak at 660 nanometers
    (A) 2-phenyl-bis-1,1-(p-dimethylaminophenyl)ethylene green. absorption peak at 660 nanometers
    (A) bis-1,1-(2-methyl-4-diethylaminophenyl)ethylene absorption peak at 770 nanometers
  (T) p-dimethylaminophenyl
    (A) 2-phenyl-bis-1,1-(p-dimethylaminophenyl)ethylene green. absorption peak at 660 nanometers
  (T) 2-methoxy-4-diethylaminophenyl
    (A) 2-methyl-bis-1,1-(p-diethylaminophenyl)ethylene blue-green. absorption peak at 630 nanometers
    (A) bis-1,1-(p-methoxyphenyl)ethylene orange, absorption peak at 600 nanometers
    (A) bis-1,1-(2-methyl-4-diethylaminophenyl)ethylene green. absorption peak at 750 nanometers
    (A) 2-carbethoxy-bis-1,1-(p-dimethylaminophenyl)ethylene olive. absorption peak at 650 nanometers
  (T) 1-(N,4'-dimethyl-2-methoxydiphenylamino)
    (A) bis-1,1-(p-methoxyphenyl)ethylene red. absorption peak at 570 nanometers
  also (T) 2-butoxy-4-diethylaminophenyl
    also (A) 2-methyl-bis-1,1-(p-dipropylaminophenyl)ethylene
    also (A) bis-1,1-(2-methyl-4-diethylaminophenyl)ethylene
  (T) 2-methoxy-4-cyclohexylaminophenyl
    (A) bis-1,1-(2-methyl-4-diethylaminophenyl)ethylene green. absorption peak at 725 nanometers
    (A) bis-1,1-(p-methoxyphenyl)ethylene yellow. absorption peak at 600 nanometers
    (A) 2-carbethoxy-bis-1,1-(p-dimethylaminophenyl)ethylene green. absorption peak at 650 nanometers
  also (T) p-phenylaminophenyl
    also (A) bis-1,1-(p-phenylaminophenyl)ethylene
  also (T) benzylaminophenyl
    also (A) bis-1,1-(p-benzylaminophenyl)ethylene
  (T) 2-methoxy-4-dimethylaminophenyl
    (A) 2-phenyl-bis-1,1-(p-dimethylaminophenyl)ethylene yellow-blue. absorption peak at 660 nanometers
  (T) 1-(N,4'-dimethyl-2-methoxydiphenylamino)
    (A) 2-carbethoxy-bis-1,1-(p-dimethylaminophenyl)ethylene green. absorption peak at 650 nanometers
    also (A) bis-1,1-(2-methyl-4-diethylaminophenyl)ethylene
also (I) 2,3-naphthalene dicarboxylic acid anhydride
also (I) 1,8-naphthalene dicarboxylic acid anhydride
also (I) 4-nitro-1,8-naphthalene dicarboxylic acid anhydride
also (I) 3-nitro-phthalic anhydride

EXAMPLE 2

Preparation of 3-(2-methoxy-4-diethylaminophenyl)-3[1-(dimethylaminophenyl)-1-(1-ethyl-2-methylindol-3-yl)ethylene-2]-4,5,6,7-tetrachlorophthalide.

This discloses an example of a compound of this invention which can be made by using a carbinol as well as by using an ethylene base. A mixture of 930 milligrams of 2-(2-methoxy-4-diethylaminobenzoyl)-3,4,5,6-tetrachlorobenzoic acid, 754 milligrams of 1,1-(p-dimethylaminophenyl) (1-ethyl-2-methyl-indol-3-yl) ethanol and 5 milliliters of acetic anhydride is refluxed one-half hour. The reaction mixture is cooled and extracted with a mixture of toluene and dilute ammonia. The toluene portion of the extract is washed with dilute ammonia, washed with water, dried and evaporated. The residue is washed with petroleum ether and then is dissolved in toluene. Petroleum ether is added to the toluene solution to precipitate the product. The solid is separated by filtration and recrystallized twice from toluene-petroleum ether. The purified product exhibits a melting point of 157°–158° centigrade, resolidifies and remelts at 199°–200° centigrade. A solution of the product imparts a blue-green color to paper coated with phenolic resin. A reflectance spectrum of the blue-green color has an absorption peak at about 758 nanometers.

Example 2, Summarized.

(I) 3,4,5,6-tetrachlorophthalic anhydride
  (T) 2-methoxy-4-diethylaminophenyl
    (A) 1-(p-dimethylaminophenyl)-1-(1-ethyl-2-methylindol-3-yl)ethylene blue green. absorption peak at 758 nanometers.
(I) phthalic anhydride
  (T) 2-methoxy-4-diethylaminophenyl
    (A) bis-1,1-(p-diethylaminophenyl)ethylene green-blue. absorption peak at 770 nanometers.

EXAMPLE 3

Preparation of 3-(4-dimethylaminophenyl)-3-[bis-1,1-(p-dimethylaminophenyl)-ethyleno-2]-6-dimethylaminophthalide.

The keto-acid for this example is 2-(4-dimethylaminobenzoyl)-5-dimethylaminobenzoic acid. A solution of 13.0 grams of the keto-acid, 15.0 grams of bis-1,1-(p-dimethylaminophenyl)ethylene (moiety A, wherein X and Y are p-dimethylaminophenyl and Z is hydrogen), and 100 milliliters of acetic anhydride is stirred for about 1 hour at about 54° centigrade. The reaction mixture is poured into ice and ammonia and the product is extracted using toluene. The toluene solution is washed with saturated aqueous sodium sulfate solution; and is then filtered and the toluene evaporated. The residue is chromatographed and the product exhibits a melting point of 155°–158° centigrade. After further purification by recrystallization from toluene-petroleum ether, the material exhibits a melting point of 157°–159° centigrade. A solution of that product imparts a dark blue color to paper coated with a phenolic resin or silton clay or a combination of the two. A reflectance spectrum of the blue color has an absorption peak at about 770 nanometers. The calculated analysis for $C_{36}H_{40}N_4O_2$, the title compound is C, 77.24%; H, 7.12%; and N, 9.85%. Found, on analysis, C, 77.11%; H, 7.19%; and N, 9.99%.

Example 3, Summarized.

(I) 4-dimethylaminophthalic anhydride
 (T) p-dimethylaminophenyl
  (A) bis-1,1-(p-dimethylaminophenyl)ethylene blue. absorption peak at 770 nanometers
  (A) bis-1,1-(2-methyl-4-diethylaminophenyl)ethylene blue. absorption peak at 770 nanometers
  (A) 2-phenyl-bis-1,1-(p-dimethylaminophenyl)ethylene blue. absorption peak at 660 nanometers
  (A) 2-carbethoxy-bis-1,1-(p-dimethylaminophenyl)ethylene absorption peaks at 655 and 590 nanometers
  (A) 2-methyl-bis-1,1-(p-diethylaminophenyl)ethylene green. absorption peak at 650 nanometers
  (A) bis-1,1-(p-methoxyphenyl)ethylene blue. absorption peak at 675 nanometers
 also (I) 4-di-t-butylamino phthalic anhydride and 4-dihexylaminophthalic anhydride
 also (T) p-diethylaminophenyl
 also (T) p-aminophenyl
 also (T) 2-hexyl-4-dihexylaminophenyl
  also (A) 2-phenyl-bis-1,1-(p-dimethylaminophenyl)ethylene
  also (A) 2-carbobutoxy-bis-1,1-(p-dimethylaminophenyl)ethylene
  also (A) bis-1,1-(2,4-di-dimethylaminophenyl)ethylene
  also (A) bis-1,1-(2-methylamino-4-dimethylaminophenyl)ethylene
  also (A) bis-1,1-(2-amino-4-dimethylaminophenyl)ethylene
  also (A) bis-1,1-(2-acetamino-4-dimethylamiophenyl)ethylene

EXAMPLE 4

Preparation of 3-(4-dimethylaminophenyl)-3-[bis-1,1-(p-dimethylaminophenyl)-ethyleno-2]-4,5,6,7-tetrachlorophthalide.

The keto acid for this example is 2-(4-dimethylaminobenzoyl)-3,4,5,6-tetrachlorobenzoic acid and it is substituted mol-for-mol for the keto acid of Example 3, above. The conditions and other materials remain the same from Example 3. The keto acid is also prepared from phthalic anhydride which is mono-, di-, and tri-halo substituted rather than tetra-substituted; and bromine can be used rather than chlorine.

Example 4, Summarized.

(I) 3,4,5,6-tetrachlorophthalic anhydride
 (T) p-dimethylaminophenyl
  (A) bis-1,1-(p-dimethylaminphenyl)ethylene green-blue. absorption peak at 770 nanometers
  (A) 2-methyl-bis-1,1-(p-diethylaminophenyl)ethylene blue. absorption peak at 640 nanometers
  (A) 2-phenyl-bis-1,1-(p-dimethylaminophenyl)ethylene green. absorption peak at 660 nanometers
  (A) 2-carbethoxy-bis-1,1-(p-dimethylaminophenyl)ethylene green. absorption peak at 675 nanometers
  (A) bis-1,1-(2-methyl-4-diethylaminophenyl)ethylene green. absorption peak at 795 nanometers
  (A) bis-1,1-(p-methoxyphenyl)ethylene blue. absorption peak at 670 nanometers
 also (T) 2-chloro-4-diethylaminophenyl
 also (T) p-diethylaminophenyl
 (T) 2-methoxy-4-diethylaminophenyl
  (A) 2-methyl-bis-1,1-(p-diethylaminophenyl)ethylene green. absorption peak at 650 nanometers
  (A) bis-1,1-(2-methyl-4-diethylaminophenyl)ethylene green. absorption peak at 770 nanometers
  (A) bis-1,1-(p-methoxyphenyl)ethylene green. absorption peak at 660 nanometers
  (A) 2-carbethoxy-1,1-(p-dimethylaminophenyl)ethylene green. absorption peak at 650 nanometers

EXAMPLE 5

Preparation of 1-(2-chloro-4-diethylaminophenyl)-1-[bis-1,1-(p-dimethylaminophenyl)-ethyleno-2]-1-[H]-3-[H]-furo[3,4-b]-quinoxalin-3-one.

The keto acid for this example is 2-(2-chloro-4-diethylaminobenzoyl)-3-quinoxalinic acid; and it is disclosed as Preparation C of U.S. Pat. application Ser. No. 468,112, filed May 8, 1974. Reaction of that keto acid with an appropriate ethylene base, as previously described above, results in compounds of this invention. Reaction with bis-1,1-(p-dimethylaminophenyl)ethylene results in the title compound.

Example 5, Summarized.

(I) quinoxalinic anhydride
 (T) 2-chloro-4-diethylaminophenyl
  (A) bis-1,1-(p-dimethylaminophenyl)ethylene yellow. absorption peak at 700 nanometers
  (A) bis-1,1-(2-methyl-4-diethylaminophenyl)ethylene yellow. absorption peak at 690 nanometers
 also (T) 2-hexoxy-4-dimethylaminophenyl
 also (T) 2-phenyl-4-dimethylaminophenyl
  also (A) 2-hexyl-bis-1,1-(p-diethylaminophenyl)ethylene
  also (A) 2-phenyl-bis-1,1-(p-diethylaminophenyl)ethylene
  also (A) bis1,1-(pyrrol-3-yl)ethylene and bis-1,1,-(pyrrol-2-yl)ethylene
  also (A) bis-1,1,-(indol-3-yl)ethylene

EXAMPLE 6

Preparation of 3-(4-dimethylaminophenyl)-3-[(4-dimethylaminophenyl)ethyleno-2[-6-dimethylaminophthalide.

As a general rule, either carbinol compounds or the corresponding ethylene bases can be used to react with keto acids under the same or similar reaction conditions, in an anhydride reaction medium. In this example, 1.55 grams of 2-(p-dimethylaminobenzoyl)-4-dimethylaminobenzoic acid and 0.82 grams of p-dimethylaminophenylmethyl carbinol are stirred together in 10 milliliters of acetic anhydride for two hours at about 56 degrees centigrade. The benzoic keto acid can, for example, be made from a mol-for-mol combination of p-dimethylaminophthalic anhydride (I) and N,N-dimethylaniline (T), as previously described. As previously, the system is extracted with toluene, dried using sodium sulfate, and the toluene is evaporated. The product is isolated using chromatography and a solution of the product imparts a blue color to paper coated with a phenolic resin or silton clay or a combination of the two. A reflectance spectrum of the blue color has an absorption peak at 735 nanometers.

This example is also conducted using p-dimethylaminophenyl ethylene, 2-methyl-1-(p-dimethylaminophenyl)ethylene, and 2-phenyl-1-(p-dimethylaminophenyl)ethylene.

Example 6, Summarized (I) p-dimethylaminophthalic anhydride
  (T) p-dimethylaminophenyl
    (A) p-dimethylaminophenyl ethylene blue. absorption peak at 735 nanometers
    also (A) 1-(p-dimethylaminophenyl)-1-(methoxyphenyl)ethylene
    (A) 2-bromo-1-(p-dimethylaminophenyl)ethylene blue. absorption shoulder at 830 nanometers, peak at 730 nanometers
also (I) p-di-t-butylaminophthalic anhydride
also (I) 3,4,5,6-tetrabromophthalic anhydride
also (I) 3-methyl phthalic anhydride and 4-butyl phthalic anhydride and 3-propyl-5-ethyl phthalic anhydride
(I) 3,4,5,6-tetrachlorophthalic anhydride
  (T) p-dimethylaminophenyl
    (A) p-dimethylaminophenylethylene green. absorption peak at 760 nanometers
    (A) 2-bromo-1-(p-dimethylaminophenyl)ethylene green. absorption peaks at 770 and 880 nanometers
    also (A) p-di-isopentylaminophenylethylene
    also (A) 1-(p-diisopentylaminophenyl)-1-(carbopentoxy)ethylene
(I) phthalic anhydride
  (T) p-dimethylaminophenyl
    (A) p-dimethylaminophenylethylene green. absorption peak at 740 nanometers
  (T) p-diethylaminophenyl
    (A) p-dimethylaminophenylethylene green. absorption peak at 740 nanometers
    (A) 2-bromo-1-(p-dimethylaminophenyl)ethylene green. absorption peak at 730 nanometers
    also (A) 2-isopropyl-1-(p-diethylaminophenyl)ethylene
    also (A) 1-(p-diethylaminophenyl)-1-(nitrophenyl)ethylene
    also (T) 2-dimethylamino-4-diethylaminophenyl
    also (T) 2-butylamino-4-dimethylaminophenyl
    also (T) 2-amino-4-dimethylaminophenyl
    also (T) 2-acetamino-4-dimethylaminophenyl
    also (T) 2-bromo-4-dimethylaminophenyl
(I) quinoxalinic anhydride
  (T) 2-chloro-4-diethylaminophenyl
    (A) 2-bromo-1-(p-dimethylaminophenyl)ethylene orange. broad absorption peak
  (T) 2-methyl-4-diethylaminophenyl
    (A) 2-bromo-1-(p-dimethylaminophenyl)ethylene broad absorption peak
  (T) 2-ethoxy-4-dimethylaminophenyl
    (A) 2-bromo-1-(p-dimethylaminophenyl)ethylene absorption peak at 625 nanometers
    also (T) 2-hexoxy-4-dimethylaminophenyl

EXAMPLE 7

Preparation of 3-(1-ethyl-2-methylindol-3-yl)-3-[bis-1,1,-(p-dimethylaminophenyl)ethyleno-2]-phthalide.

In this example, 6.17 grams of 1-ethyl-2-methyl-3-(2-carboxybenzoyl)indole, 5.3 grams of bis-1,1-(p-dimethylaminophenyl)ethylene, and 20 milliliters of acetic anhydride are stirred for about 80 minutes at about 65 degrees centigrade. The keto acid of this example can be prepared from a combination of phthalic anhydride with 1-ethyl-2-methylindole alone or in the presence of aluminum chloride. The title compound is isolated in the manner previously described and imparts a blue-green color to paper coated with a phenolic resin or silton clay or a combination of the two. A reflectance spectrum of the blue-green color has an absorption peak at 690 nanometers.

This example is also conducted using p-dimethylaminophenylethylene, 2-methyl-1-(p-dimethylaminophenyl)ethylene, bis-1,1,-(2-methyl-4-diethylaminophenyl)ethylene, and 2-phenyl-1-(p-dimethylaminophenyl)ethylene.

Example 7, Summarized.

(I) phthalic anhydride
  (T) 1-ethyl-2-methylindolyl
    (A) bis-1,1-(p-dimethylaminophenyl)ethylene blue-green. broad absorption peak from 575 to 750 nanometers
    (A) bis-1,1,-(2-methyl-4-diethylaminophenyl)ethylene green. absorption peak at 720 nanometers
    (A) 2-methyl-bis-1,1-(p-diethylaminophenyl)ethylene green. absorption peak at 650 nanometers
    (A) bis-1,1-(p-methoxyphenyl)ethylene red. absorption peak at 570 nanometers
    (A) p-dimethylaminophenylethylene green. absorption peak at 690 nanometers
    (A) 2-bromo-4-dimethylaminophenylethylene blue. absorption peaks at 700 and 800 nanometers
  also (T) 1-ethyl-2-methyl-1-H-benz[G]indolyl
  also (T) 2-phenylindolyl
  also (T) 1-phenyl-2-methylindolyl
  also (T) 1-phenylcarbazol-4-yl
  also (T) 7-ethylcarbazol-4-yl
    also (A) p-diethylaminophenylethylene
(I) 3,4,5,6-tetrachlorophthalic anhydride
  (T) 1-ethyl-2-methylindolyl
    (A) bis-1,1,-(p-dimethylaminophenyl)ethylene blue. absorption peak at 645 nanometers
    (A) bis-1,1-(p-methoxyphenyl)ethylene red. absorption peak at 560 nanometers
    (A) p-dimethylaminophenylethylene red. absorption peak at 740 nanometers
    (A) 2-bromo-4-dimethylaminoethylene brown. absorption peak at 700 nanometers
    (A) bis-1,1-(2-methyl-4-diethylaminophenyl)ethylene green. absorption peak at 720 nanometers
  also (T) 1-ethyl-2-methyl-5-hexoxyindolyl
  also (T) 1-hexyl-2-ethylindolyl
    also (A) 2-bromo-1-(p-dimethylaminophenyl)ethylene also (I) 3,4,5,6-tetrabromophthalic anhydride
  (T) 1-ethyl-2-methylindolyl
    (A) 2-methyl-bis-1,1-(p-diethylaminophenyl)ethylene green. absorption peak at 650 nanometers
    (A) 2-bromo-4-dimethylaminoethylene yellow-green. absorption peak at 830 nanometers
  also (T) 2-pentylindolyl
also (I) 3,4-pyridinedicarboxylic acid anydride
(I) 2,3-pyrazinedicarboxylic acid anhydride
  (T) 1-ethyl-2-methylindolyl
    (A) 2-bromo-4-dimethylaminophenylethylene green. absorption peak at 700 nanometers
    (A) bis-1,1-(2-methyl-4-diethylaminophenyl)ethylene green. absorption peak at 700 nanometers
(I) quinoxalinic anhydride
  (T) 1-ethyl-2-methylindolyl
    (A) bis-1,1-(p-dimethylaminophenyl)ethylene blue. absorption peaks at 645 and 700 nanometers
    (A) 2-methyl-bis-1,1-(p-diethylaminophenyl)ethylene green. absorption peak at 650 nanometers
    (A) 2-bromo-4-dimethylaminophenylethylene rust. absorption peak at 830 nanometers

EXAMPLE 8

Preparation of 3-(p-diethylaminophenyl)-3-[1-(N-carbazolyl)ethyleno-2]phthalide.

In this example a mol-for-mol combination of phthalic anhydride (I) and N,N-diethylaniline (T) are reacted, as disclosed previously, to yield the keto acid (II). The keto acid is similarly reacted with N-vinyl carbazole to yield the title compound. The title compound imparts a blue-yellow color to paper coated with a phenolic resin or silton clay or a combination of the two. A reflectance spectrum of the blue-yellow color has an absorption peak at 630 nanometers.

This example is also conducted using N-vinylindole and N-vinylpyrrole.

Example 8, Summarized.

(I) phthalic anhydride
  (T) p-diethylaminophenyl
    (A) N-vinylcarbazole blue-yellow. absorption peak at 630 nanometers
  (T) 2-methoxy-4-diethylaminophenyl
    (A) N-vinylcarbazole blue-yellow. absorption peak at 610 nanometers
  also (T) p-dimethylaminophenyl
  also (T) 2-ethoxy-4-dimethylaminophenyl
  (T) 1-ethyl-2-methylindol-3-yl
    (A) N-vinylcarbazole neutral. absorption peaks at 680 and 770 nanometers
(I) 3,4,5,6-tetrachlorophthalic anhydride
  (T) p-dimethylaminophenyl
    (A) N-vinylcarbazole blue-yellow. absorption peak at 750 nanometers
  (T) 2-methoxy-4-diethylaminophenyl
    (A) N-vinylcarbazole green. absorption peak at 740 nanometers
  also (T) p-dimethylaminophenyl
  also (T) 2-ethoxy-4-dimethylaminophenyl
  (T) 1-ethyl-2-methylindol-3-yl
    (A) N-vinylcarbazole blue. broad absorption peak
(I) 2,3-pyridinedicarboxylic acid anhydride
  (T) 1-ethyl-2-methylindol-3-yl
    (A) N-vinylcarbazole pink. broad absorption peak
(I) 4-dimethylaminophthalic anhydride
  (T) p-dimethylaminophenyl
    (A) N-vinylcarbazole blue. absorption peak at 640 nanometers The gist of this example is the use of N-vinylcarbazole, N-vinylindole and N-vinylpyrrole in the molecule of this invention; and any of the (I) components and any of the (T) components disclosed herein are eligible.

EXAMPLE 9

Preparation of chromogenic compounds based on keto-glutaric anhydride. Either of $\alpha$-keto-glutaric anhydride or $\beta$-keto-glutaric anhydride can be used.

The keto-glutaric anhydride (I) is reacted mol-for-mol with a compound such as 1-ethyl-2-methylindole (T) in the presence of a catalyst, as previously disclosed, to yield keto-acid (II).

The keto-acid (II) is further reacted, in mol-for-mol amounts, with an appropriate ethylene base such as bis-1,1-(dimethylaminophenyl)ethylene to yield a chromogenic compound of this invention.

Mol equivalents of keto-glutaric anhydride (I) and previously-disclosed N,N-dialkylaniline; alkoxy-N,N-dialkylaniline; phenyl-N,N-dialkylaniline; alkyl-N,N-dialkylaniline; chloro- or bromo-N,N-dialkylaniline; indole; alkyl-substituted indole; or phenyl-substituted indole, and the like (T, as a group) yield a keto acid additionally reactive with the previously-disclosed vinyl compounds (A) such as bis-1,1-(p-diethylaminophenyl)ethylene, 2-phenyl-bis-1,1-(p-dimethylaminophenyl)ethylene, N-vinylcarbazole, and the like.

EXAMPLE 10

Preparation of chromogenic compounds based on homophthalic anhydride.

Homophthalic anhydride (I) can be reacted mol-for-mol with a compound such as 1-ethyl-2-methylindole (T) in the presence of a catalyst, as previously disclosed, to yield keto-acid (II).

The keto-acid (II) is further reacted, in mol-for-mol amounts, with an appropriate ethylene base such as bis-1,1-(dimethylaminophenyl)ethylene to yield a chromogenic compound of this invention.

Mol equivalents of homophthalic anhydride (I) and previously-disclosed N,N-dialkylaniline; alkoxy-N,N-dialkylaniline; phenyl-N,N-dialkylaniline; alkyl-N,N-dialkylaniline; chloro or bromo-N,N-dialkylaniline; indole; alkyl-substituted indole; or phenyl-substituted indole, and the like, (T, as a group) yield a keto acid additionally reactive with the previously-disclosed vinyl compounds (A) such as bis-1,1-(p-diethylaminophenyl)ethylene, 2-phenyl-bis-1,1-(p-dimethylaminophenyl)ethylene, N-vinylcarbazole, and the like.

EXAMPLE 11

Preparation of chromogenic compounds based on biphenyl-4,4'-dicarboxylic anhydride.

The biphenyl-4,4'-dicarboxylic anhydride (I) can be reacted mol-for-mol with a compound such as 1-ethyl-2-methylindole (T) in the presence of a catalyst, as previously disclosed, to yield keto-acid (II).

The keto-acid (II) is further reacted, in mol-for-mol amounts, with an appropriate ethylene base such as bis-1,1-(dimethylaminophenyl)ethylene to yield a chromogenic compound of this invention.

Mol equivalents of biphenyl-4,4'-dicarboxylic anhydride (I) and previously-disclosed N,N-dialkylaniline; alkoxy-N,N-dialkylaniline; phenyl-N,N-dialkylanaline; alkyl-N,N-dialkylaniline; chloro- or bromo-N,N-dialkylaniline; indole; alkyl-substituted indole; or phenyl-substituted indole (T, as a group) yield a keto acid additionally reactive with the previously-disclosed vinyl compounds (A) such as bis-1,1-(p-diethylaminophenyl)ethylene, 2-phenyl-bis-1,1-(p-dimethylaminophenyl)ethylene, N-vinylcarbazole, and the like.

Preparation of 3-(p-diethylaminophenyl)-3-[1-(dimethylaminophenyl)-1-(1-ethyl-2-methylindol-3-yl)ethyleno-2]-4,5,6,7-tetrachlorophthalide.

Preparation of this compound commences at (II), the keto acid. A mixture of 1.15 grams of 2-(4-diethylaminobenzoyl)-3,4,5,6-tetrachlorobenzoic acid, 3.27 grams of 1-(p-dimethylaminophenyl)-1-(1-ethyl-2-methylindol-3-yl) ethylene and 5 milliliters of acetic anhydride is refluxed overnight. The reaction mixture is added to a mixture of toluene, ice and ammonia. The toluene phase is separated, the aqueous phase is extracted with additional toluene and the toluene phases are combined. The toluene solution is washed with saturated aqueous sodium sulfate solution, and is then filtered and the toluene evaporated. Crystalline material is isolated by fractional crystallization. After further purification by recrystallizations from toluene-petroleum ether, the material exhibits a melting point of 211.5 – 212.0 degrees centigrade. A solution of that product imparts a blue-green color to paper coated with a phenolic resin or a blue color to paper coated with silton clay. A reflectance spectrum of the blue-green color has an absorption peak at about 750 nanometers. The calculated analysis for $C_{39}H_{37}N_3O_2Cl_4$, the title compound is C, 64.92%; H, 5.17%; N, 5.82%; and Cl, 19.66%. Found, on analysis, C. 65,02%; H, 5.31%; N, 5.70%; and Cl, 19.43%.

Example 12, Summarized (I) 3,4,5,6-tetrachlorophthalic anhydride
 (T) p-diethylaminophenyl
  (A) 1-(p-dimethylaminophenyl)-1-(1-ethyl-2-methylindol-3-yl)ethylene blue-green. absorption peak at 750 nanometers
  (A) 1-(p-dimethylaminophenyl)-1-(1-ethyl-2-methylindol-3-yl)ethylene blue. absorption peak at 747 nanometers
Also (I) phthalic anhydride
 (T) p-diethylaminophenyl
  (A) 1-(p-dimethylaminophenyl)-1-(1-ethyl-2-methylindol-3-yl)ethylene blue. absorption peak at 743 nanometers
 (T) 2-methoxy-4-diethylaminophenyl
  (A) 1-(p-dimethylaminophenyl)-1-(1-ethyl-2-methylindol-3-yl)ethylene green. absorption peak at 727 nanometers
 (T) 2-methoxy-4-(N-methyl-N-4-tolylamino)phenyl
  (A) 1-(p-dimethylaminophenyl)-1-(1-ethyl2-methylindol-3-yl)ethylene blue. absorption peak at 714 nanometers
 (T) 2-methoxy-4-cyclohexylaminophenyl
  (A) 1-(p-dimethylaminophenyl)-1-(1-ethyl-2 -methylindol-3-yl)ethylene blue. absorption peak at 717 nanometers
 (T) 2-butoxy-4-diethylaminophenyl
  (A) 1-(p-dimethylaminophenyl)-1-(1-ethyl-2-methylindol-3-yl)ethylene blue. absorption peak at 727 nanometers
 (T) p-morpholinophenyl
  (A) 1-(p-dimethylaminophenyl)-1-(1-ethyl-2-methylindol-3-yl)ethylene blue. absorption peak at 727 nanometers (I) 4-dimethylaminophthalic anhydride
 (T) p-dimethylaminophenyl
  (A) 1-(p-dimethylaminophenyl)-1-(1-ethyl-2-methylindol-3-yl)ethylene blue. absorption peak at 743 nanometers
(I) 2,3-pyridine dicarboxylic acid anhydride
 (T) 2-ethoxy-4-diethylaminophenyl
  (A) 1-(p-dimethylaminophenyl)-1-(1-ethyl-2-methylindol-3yl)ethylene green. absorption peak at 750 nanometers
 (T) kairol-6-yl
  (A) 1-(p-dimethylaminophenyl)-1-(1-ethyl-2-methylindol-3-yl)ethylene green. absorption peak at 770 nanometers
 (T) julolidin-9-yl
  (A) 1-(p-dimethylaminophenyl)-1-(1-ethyl-2-methylindol-3-yl)ethylene green. absorption peak at 800 nanometers
(I) 2,3-quinilinedicarboxylic acid anhydride
 (T) 2-ethoxy-4-diethylaminophenyl
  (A) 1-(p-dimethylaminophenyl)-1-(1-ethyl-2-methylindol-3-yl)ethylene green. absorption peak at 758 nanometers
(I) 2,3-quinoxalinedicarboxylic acid anhydride
 (T) 2-chloro-4-diethylaminophenyl
  (A) 1-(p-dimethylaminophenyl)-1-(1-ethyl-2-methylindol-3-yl)ethylene green. absorption peak at 690 nanometers

EXAMPLE 13

Preparation of 3-(p-diethylaminophenyl)-3-[1,1-bis(p-dimethylaminophenyl)ethyleno-2]-4,5,6,7-tetrachlorophthalide.

A mixture of 4.35 grams 2-(4-diethylaminobenzoyl)-3,4,5,6-tetrachlorobenzoic acid, 2.66 grams of bis-1,1-(p-dimethylaminophenyl)ethylene and 20 milliliters of acetic anhydride is heated at 90 degrees centigrade for 125 minutes. The reaction mixture is cooled and added to a mixture of toluene, ice and ammonia and allowed to stand overnight. The solid, separated from the liquid by decantation, is recrystallized repeatedly from toluene petroleum ether and then from toluene yielding a material which exhibits a melting point of 215.5 – 217 degrees centigrade. A solution of that product imparts a green-blue color to paper coated with a phenolic resin. A reflectance spectrum of the green-blue color has an absorption peak at about 763 nanometers. The calculated analysis for $C_{36}H_{35}N_3Cl_4O_2$, the title compound, is C, 63,26%; H, 5.16%; N, 6.15%; and Cl, 20.75%. Found, on analysis, C, 63.59%; H, 5.23%; N, 6.03%; and Cl, 20.51%.

Example 13, Summarized.

(I) 3,4,5,6-tetrachlorophthalic anhydride
 (T) p-diethylaminophenyl
  (A) bis-1,-(p-dimethylaminophenyl)ethylene green-blue. absorption peak at 763 nanometers
  (A) bis-1,1-(2-methyl-4-diethylaminophenyl)ethylene red. absorption peak at 794 nanometers
  (A) 2-methyl-bis-1,1-(p-diethylaminophenyl)ethylene green. absorption peak at 650 nanometers.
  (A) 1-(p-piperidinophenyl)-1-(p-dimethylaminophenyl) ethylene green. absorption peak at 769 nanometers
  (A) bis-1,1-(p-piperidinophenyl)ethylene green. absorption peak at 781 nanometers
  (A) 1-phenyl-1-(p-dimethylaminophenyl)ethylene red. absorption peak at 809 nanometers (A) bis-1,1-(p-methoxyphenyl)ethylene green. absorption peak at 667 nanometers
(A) 1-(p-dimethylaminophenyl)ethylene green. absorption peak at 735 nanometers
(T) 2-methoxy-4-diethylaminophenyl
  (A) bis-1,1-(2-methyl-4-diethylaminophenyl)ethylene red. absorption peak at 769 nanometers
  (A) 2-methyl-bis-1,1-(p-diethylaminophenyl)ethylene green. absorption peak at 645 nanometers
  (A) 1-(p-piperidinophenyl)-1-(p-dimethylaminophenyl)ethylene green. absorption peak at 758 nanometers
  (A) bis-1,1-(p-piperidinophenyl)ethylene green. absorption peak at 758 nanometers
  (A) 1-phenyl-1-(p-dimethylaminophenyl)ethylene red. absorption peak at 775 nanometers
  (A) bis-1,1-(p-methoxyphenyl)ethylene green. absorption peak at 658 nanometers
(I) phthalic anhydride
  (T) p-diethylaminophenyl
    (A) bis-1,1-(2-methyl-4-diethylamino-phenyl)ethylene green. absorption peak at 758 nanometers
    (A) 2-methyl-bis-1,1-(p-diethylaminophenyl)ethylene blue. absorption peak at 640 nanometers
    (A) 1-(p-piperidinophenyl)-1-(p-dimethylaminophenyl)ethylene green. absorption peak at 752 nanometers
    (A) bis-1,1-(p-piperidinophenyl)ethylene blue. absorption peak at 758 nnometers
    (A) 1-phenyl-1-(p-dimethylaminophenyl)ethylene red. absorption peak at 775 nanometers
    (A) 1-(p-dimethylaminophenyl)ethylene green. absorption peak at 740 nanometers
  (T) 2-methoxy-4-diethylaminophenyl
    (A) bis-1,1-(2-methyl-4-diethylaminophenyl)ethylene orange. absorption peak at 746 nanometers
    (A) 2-methyl-bis-1,1-(p-diethylaminophenyl)ethylene green, absorption peak at 640 nanometers
    (A) 1-(p-piperidinophenyl)-1-(p-dimethylaminophenyl)ethylene blue, absorption peak at 725 nanometers
    (A) bis-1,1-(p-piperidinophenyl)ethylene green. absorption peak at 774 nanometers
    (A) 1-phenyl-1-(p-dimethylaminophenyl)ethylene green. absorption peak at 751 nanometers
    (A) 1-(p-dimethylaminophenyl)ethylene green. absorption peak at 714 nanometers
  (T) 2-butoxy-4-diethylaminophenyl
    (A) 2-methyl-bis-1,1-(p-diethylaminophenyl)ethylene. absorption peak at 645 nanometers
    (A) 1-(p-piperidinophenyl)-1-(p-dimethylaminophenyl)ethylene blue. absorption peak at 735 nanometers
    (A) bis-1,1-(p-piperidinophenyl)ethylene blue. absorption peak at 752 nanometers
    (A) 1-phenyl-1-(p-dimethylaminophenyl)ethylene green. absorption peak at 746 nanometers
    (A) 1-(p-dimethylaminophenyl)ethylene green. absorption peak at 714 nanometers
  (T) 2-methoxy-4-cyclohexylaminophenyl
    (A) bis-1,1-(2-methyl-4-diethylaminophenyl)ethylene red. absorption peak at 714 nanometers
    (A) 2-methyl-bis-1,1-(p-diethylaminophenyl)ethylene. absorption peak at 645 nanometers
    (A) 1-(p-piperidinophenyl)-1-(p-dimethylaminophenyl)ethylene blue. absorption peak at 719 nanometers
    (A) bis-1,1-(p-piperidinophenyl)ethylene blue. absorption peak at 725 nanometers
    (A) 1-phenyl-1-(p-dimethylaminophenyl)ethylene red. absorption peak at 746 nanometers
    (A) 1-(p-dimethylaminophenyl)ethylene green. absorption peak at 709 nanometers
  (T) 2-methoxy-4-(N-methyl-N-4-tolylamino)phenyl
    (A) 2-methyl-bis-1,1-(p-diethylaminophenyl)ethylene blue. absorption peak at 645 nanometers
    (A) 1-(piperidinophenyl)-1-(p-dimethylaminophenyl)ethylene blue. absorption peak at 725 nanometers
    (A) bis-1,1-(p-piperidinophenyl)ethylene blue. absorption peak at 741 nanometers
    (A) 1-phenyl-1-(p-dimethylaminophenyl)ethylene red. absorption peak at 657 nanometers
  (T) p-morpholinophenyl
    (A) 2-methyl-bis-1,1-(p-diethylaminophenyl)ethylene blue. absorption peak at 645 nanometers
    (A) 1-(p-piperidinophenyl)-1-(p-dimethylaminophenyl)ethylene blue. absorption peak at 654 nanometers
    (A) bis-1,1-(p-piperidinophenyl)ethylene blue. absorption peak at 678 nanometers
    1-phenyl-1-(p-dimethylaminophenyl)ethylene red. absorption peak at 657 nanometers
(I) 4-dimethylaminophthalic anhydride
  (T) p-dimethylaminophenyl
    (A) 2-methyl-bis-1,1-(p-diethylaminophenyl)ethylene green. absorption peak at 640 nanometers
    (A) 1-(p-piperidinophenyl)-1-(p-dimethylaminophenyl)ethylene blue. absorption peak at 758 nanometers
    (A) bis-1,1-(p-piperidinophenyl)ethylene blue. absorption peak at 758 nanometers
    (A) 1-phenyl-1-(p-dimethylaminophenyl)ethylene green. absorption peak at 657 nanometers
    (A) 1-(p-dimethylaminophenyl)ethylene blue. absorption peak at 725 nanometers
    (A) bis-1,1-(p-methoxyphenyl)ethylene blue. absorption peak at 658 nanometers
(I) 2,3-pyridinedicarboxylic acid anhydride
  (T) 2-ethoxy-4-diethylaminophenyl
    (A) bis-1,1-(p-piperidinophenyl)ethylene green. absorption peak at 751 nanometers
    (A) 1-(p-piperidinophenyl)-1-(p-dimethylaminophenyl)ethylene green. absorption peak at 740 nanometers
    (A) 1-(p-dimethylaminophenyl)ethylene green. absorption peak at 730 nanometers
  (T) kairol-6-yl
    (A) bis-1,1-(p-piperidinophenyl)ethylene green. absorption peak at 781 nanometers
    (A) 1-(p-piperidinophenyl)-1-(p-dimethylaminophenyl)ethylene green. absorption peak at 775 nanometers
  (T) julolidin 9-yl
    (A) bis-1,1-(p-piperidinophenyl)ethylene green. absorption peak at 800 nanometers
    (A) 1-(p-piperidinophenyl)-1-(p-dimethylaminophenyl)ethylene green. absorption peak at 800 nanometers
(I) 2,3-quinilinedicarboxylic acid anhydride
  (T) 2-ethoxy-4-diethylaminophenyl
    (A) bis-1,1-(p-piperidinophenyl)ethylene green. absorption peak at 752 nanometers (A) 1-(p-piperidinophenyl)-1-(p-dimethylaminophenyl)ethylene green. absorption peak at 740 nanometers
(A) 1-(p-dimethylaminophenyl)ethylene green. absorption peak at 735 nanometers
(I) 2,3-quinoxalinedicarboxylic acid anhydride
 (T) 2-chloro-4-diethylaminophenyl
  (A) bis-1,1-(p-piperidinophenyl)ethylene green. absorption peak at 704 nanometers

EXAMPLE 14

Preparation of 3-(1-ethyl-2-methylindol-3-yl)-3-[1,1-bis-(p-dimethylaminophenyl)ethyleno-2]-4,5,6,7-tetrachlorophthalide.

A mixture of 4.3 grams of 2-(1-ethyl-2-methylindol-3-yl)-3,4,5,6-tetrachlorobenzoic acid, 2.66 grams of bis-1,1,-(p-dimethylaminophenyl)ethylene and 20 milliliters of acetic anhydride is heated to 71° centigrade for 174 minutes and allowed to stand over night. The solid product is collected by filtration of the reaction mixture, washed with acetic anhydride and then washed with toluene. The product is purified by recrystallizations from toluene-petroleum ether and finally from chloroform-petroleum ether. The material exhibited a melting point of 209°–210° centigrade. A solution of the product imparts a blue-green color to paper coated with a phenolic resin. A reflectance spectrum of the glue-green color has an absorption peak at about 683 nanometers.

Example 14, Summarized.
(I) 3,4,5,6-tetrachlorophthalic anhydride
 (T) 1-ethyl-2-methylindolyl
  (A) bis-1,1-(p-dimethylaminophenyl)ethylene blue-green. absorption peak at 683 nanometers
  (A) 1-(p-piperidinophenyl)-1-(p-dimethylaminophenyl)ethylene blue. absorption peak at 704 nanometers
  (A) bis-1,1-(p-piperidinophenyl)ethylene blue. absorption peak at 725 nanometers
  (A) 1-(p-dimethylaminophenyl)-1-(1-ethyl-2-methylindol-3-yl)ethylene purple. absorption peak at 699 nanometers
  (A) bis-1,1-(p-methoxyphenyl)ethylene purple. absorption peak at 549 nanometers
(I) phthalic anhydride
 (T) 1-ethyl-2-methylindolyl
  (A) 1-(p-piperidinophenyl)-1-(p-dimethylaminophenyl)ethylene blue. absorption peak at 690 nanometers
  (A) bis-1,1-(p-piperidinophenyl)ethylene blue. absorption peak at 690 nanometers
  (A) 1-(p-dimethylaminophenyl)-1-(1-ethyl-2-methylindol-3-yl)ethylene blue. absorption peak at 685 nanometers
  (A) bis-1,1-(p-methoxyphenyl)ethylene purple. absorption peak at 662 nanometers
(I) 3-nitrophthalic anhydride
 (T) 1,2-dimethylindolyl
  (A) 1-(p-piperidinophenyl)-1-(p-dimethylaminophenyl)ethylene green. absorption peak at 704 nanometers
  (A) bis-1,1-(p-piperdinophenyl)ethylene blue. absorption peak at 704 nanometers
  (A) 1-(p-dimethylaminophenyl)-1-(1-ethyl-2-methylindol-3-yl)ethylene blue. absorption peak at 699 nanometers
(I) 3,4-pyridinedicarboxylic acid anhydride
 (T) 1-ethyl-2-methylindolyl
  (A) 1-(p-piperidinophenyl)-1-(p-dimethylaminophenyl)ethylene blue. absorption peak at 690 nanometers
  (A) bis-1,1,-(p-piperidinophenyl)ethylene blue. absorption peak at 699 nanometers
  (A) 1-(p-dimethylaminophenyl)-1-(1-ethyl-2-methylindol-3-yl)ethylene blue. absorption peak at 694 nanometers
(I) 2,3-pyridinedicarboxylic acid anhydride
 (T) 1-ethyl-2-methylindolyl
  (A) 1-(p-piperidinophenyl)-1-(p-dimethylaminophenyl)ethylene green. absorption peak at 690 nanometers
  (A) bis-1,1,-(p-piperidinophenyl)ethylene green. absorption peak at 690 nanometers
(I) 2,3-pyrazinedicarboxylic acid anhydride
 (T) 1-ethyl-2-methylindolyl
  (A) 1-(p-piperidinophenyl)-1-(p-dimethylaminophenyl)ethylene green. absorption peak at 690 nanometers
  (A) bis-1,1-(p-piperidinophenyl)ethylene blue. absorption peak at 699 nanometers
(I) 2,3-quinilinedicarboxylic acid anhydride
 (T) 1-ethyl-2-methylindolyl
  (A) 1-(p-piperidinophenyl)-1-(p-dimethylaminophenyl)ethylene blue. Absorption peak at 699 nanometers
  (A) bis-1,1-(p-piperidinophenyl)ethylene green. absorption peak at 704 nanometers
(I) 2,3-quinoxalinedicarboxylic acid anhydride
 (T) 1-ethyl-2-methylindolyl
  (A) 1-(p-piperidinophenyl)-1-(p-dimethylaminophenyl)ethylene green. absorption peak at 694 nanometers
  (A) bis-1,1-(p-piperidinophenyl)ethylene green. absorption peak at 704 nanometers

What is claimed is:

1. A compound represented by a formula selected from:

(a) [structure with indole bearing $R_7$, $R_8$, connected to $C-C=C-Y$ with H, X, and $C=O$, $O$, $E$ group]

wherein E is [benzene ring], tetrachloro-substituted

[benzene ring], [nitrobenzene with $NO_2$], [pyridine ring],

[pyridine ring], [pyrazine ring],

[quinoline ring] and [quinoxaline ring];

X and Y are [p-aminophenyl with $N(R_1)(R_2)$],

-continued 4-methoxyphenyl, 4-(N-piperidino) phenyl and 4-(N-pyrrolidino)phenyl; and $R_1$, $R_2$, $R_7$ and $R_8$ are alkyl;

provided when X is

Y is X and E is ;

when X is , Y is and E is , tetrachloro-substituted ,  and ;

and when X is 4-methoxyphenyl, Y is X and

E is  and tetrachloro-substituted ;

(b)

wherein E is

, tetrachloro-substituted  and

;

X is ,

4-(N-piperidino)phenyl and 4-(N-pyrrolidino)phenyl; Y is 4-(N-piperidino)phenyl, 4-(N-pyrrolidino)phenyl, phenyl and

;

$R_1$ is hydrogen, alkyl and phenyl;
$R_2$ is alkyl and cycloalkyl;
$R_3$ is hydrogen and alkoxy having 1 to 4 carbons; and
$R_7$ and $R_8$ are alkyl;
provided when Y is phenyl or X is ;

(c)

wherein E is ,  and

;

X is ,

4-(N-piperidino)phenyl, 4-(N-pyrrolidino)phenyl; Y is any X, hydrogen and

;

$R_1$, $R_2$, $R_7$ and $R_8$ are alkyl; and
$R_3$ is hydrogen, methoxy, ethoxy and chlorine;
provided when E is or , $R_3$ is not chlorine, and additionally when Y is hydrogen or

, X is ; and when E is ,

-continued

X is , Y is 4-(N-piperidino)phenyl, 4-(N-pyrrolidino)phenyl or and R₃ is chlorine;

(d)

wherein X is

, 4-(N-piperidino)phenyl and 4-(N-pyrrolidino)phenyl; Y is hydrogen, phenyl,

; and

R₁, R₂, R₇ and R₈ are alkyl; provided when Y is

, X is ; and (e)

wherein T is kairol-6-yl and julolidin-9-yl;

, 4-(N-piperidino)phenyl and 4-(N-pyrrolidino)phenyl;

;

and R₁, R₂, R₃ and R₈ are alkyl.

2. A compound according to claim 1 having the formula, 3-(2-methoxy-4-diethylaminophenyl)-3[1-(dimethylaminophenyl)-1-(1-ethyl-2-methylindol-3-yl)ethyleno-2]-4,5,6,7-tetrachlorophthalide.

3. A compound according to claim 1 having the formula, 3-(p-diethylaminophenyl)-3-[1-(dimethylaminophenyl)-1-(1-ethyl-2-methylindol-3-yl)ethyleno-2]-4,5,6,7-tetrachlorophthalide.

4. A compound according to claim 1 having the formula, 3-(1-ethyl-2-methylindol-3-yl)-3-[1,1-bis-(p-dimethylaminophenyl)ethyleno-2]-4,5,6,7-tetrachlorophthalide.

5. A compound represented by the formula:

wherein R₁ and R₂ are alkyl.

6. A compound according to claim 5 wherein R₁ and R₂ are methyl.

7. A compound represented by the formula:

T is 4-(N-morpholino)phenyl and

;

R₁ is hydrogen, alkyl, tolyl and cyclohexyl;
R₂ is hydrogen and alkyl;
R₃ is hydrogen and alkoxy; and
R₇ and R₈ are alkyl.

8. 3-(p-diethylaminophenyl)-3-[2-methyl-bis-1,1-(p-dimethylaminophenyl)ethyleno-2] phthalide.

9. 3-(2-methoxy-4-diethylaminophenyl)-3-[2-methyl-bis-1,1-(p-diethylaminophenyl)ethyleno-2]-4,5,6,7-tetrachlorophthalide.

10. 3-[4-(N-morpholino) phenyl]-3-[2-methyl-bis-1,1-(p-diethylaminophenyl) ethyleno-2] phthalide.

* * * * *